(12) United States Patent
Bootsma

(10) Patent No.: US 10,465,152 B2
(45) Date of Patent: Nov. 5, 2019

(54) SYSTEMS AND METHODS FOR STILLAGE FRACTIONATION

(71) Applicant: POET Research, Inc., Sioux Falls, SD (US)

(72) Inventor: Jason Alan Bootsma, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 0 days.

(21) Appl. No.: 15/015,355

(22) Filed: Feb. 4, 2016

(65) Prior Publication Data

US 2016/0152931 A1 Jun. 2, 2016

Related U.S. Application Data

(62) Division of application No. 14/112,897, filed as application No. PCT/US2012/033346 on Apr. 12, 2012, now Pat. No. 9,290,728.
(Continued)

(51) Int. Cl.
*C12F 3/00* (2006.01)
*C12M 3/00* (2006.01)
(Continued)

(52) U.S. Cl.
CPC .................. *C12F 3/10* (2013.01); *A23K 1/06* (2013.01); *A23K 1/1643* (2013.01); *C10L 1/026* (2013.01);
(Continued)

(58) Field of Classification Search
CPC .......... C12M 47/00; C12M 47/10; C12F 3/00; C12F 3/10; C12F 3/06
See application file for complete search history.

(56) References Cited

U.S. PATENT DOCUMENTS 2,446,913 A 8/1948 Erlich
2,698,826 A 1/1955 Peltzer, Sr.
(Continued)

FOREIGN PATENT DOCUMENTS

WO 2010138110 12/2010
WO 2017059083 A1 4/2017

OTHER PUBLICATIONS

Office Action for Mexican Patent Application No. MX/a/2013/012195 dated Jun. 27, 2016, 2 pages.
(Continued)

*Primary Examiner* — Nathan A Bowers
(74) *Attorney, Agent, or Firm* — Kagan Binder, PLLC

(57) ABSTRACT

Systems and methods for fractionating whole stillage from an ethanol production facility are provided. Whole stillage undergoes a separation of its liquid portion (thin stillage) from the solid portion (fiber cake). In some embodiments, the solids and liquids in whole stillage may be separated utilizing a screening centrifuge. The fiber cake may be dried to generate a high fiber animal feed. The thin stillage may be provided to a three-phase separator for separation into an oil emulsion, an aqueous clarified stillage, and a protein paste. The protein paste may be dried to generate a high protein animal feed with greater than about 45% protein content. The clarified thin stillage is condensed to yield a syrup with greater than around 60% solids. The oil emulsion is subjected to a pH adjustment to liberate the oil from the emulsion, which is then separated.

10 Claims, 6 Drawing Sheets

Related U.S. Application Data

(60) Provisional application No. 61/476,702, filed on Apr. 18, 2011.

(51) Int. Cl.

| | | |
|---|---|---|
| *C12F 3/10* | (2006.01) | |
| *C11B 1/00* | (2006.01) | |
| *C10L 1/02* | (2006.01) | |
| *A23K 1/06* | (2006.01) | |
| *A23K 1/16* | (2006.01) | |
| *C12M 1/34* | (2006.01) | |
| *C12M 1/00* | (2006.01) | |

(52) U.S. Cl.
CPC ............... *C11B 1/00* (2013.01); *C12M 41/26* (2013.01); *C12M 43/00* (2013.01); *C12M 47/10* (2013.01); *C12M 47/14* (2013.01)

(56) References Cited

U.S. PATENT DOCUMENTS

| | | | |
|---|---|---|---|
| 5,250,182 A * | 10/1993 | Bento | B01D 61/58 |
| | | | 210/259 |
| 5,662,810 A | 9/1997 | Willgohs | |
| 5,795,477 A | 8/1998 | Herman et al. | |
| 6,106,673 A | 8/2000 | Walker | |
| 7,101,691 B2 | 9/2006 | Kinley et al. | |
| 7,497,955 B2 | 3/2009 | Scheimann et al. | |
| 7,601,858 B2 | 10/2009 | Cantrell et al. | |
| 7,608,729 B2 | 10/2009 | Winsness et al. | |
| 7,829,680 B1 | 11/2010 | Sander et al. | |
| 7,915,458 B2 | 3/2011 | Bruckmayer | |
| 8,103,385 B2 | 1/2012 | Macharia et al. | |
| 8,168,037 B2 | 5/2012 | Winsness | |
| 8,236,977 B2 | 8/2012 | Woods et al. | |
| 8,257,951 B2 | 9/2012 | Prevost et al. | |
| 8,679,353 B2 | 3/2014 | Winsness | |
| 8,778,433 B2 | 7/2014 | Lee | |
| 8,813,973 B2 | 8/2014 | Lee et al. | |
| 8,956,460 B2 | 2/2015 | Ahmed et al. | |
| 8,962,059 B1 | 2/2015 | Froderman et al. | |
| 8,986,551 B2 | 3/2015 | Kohl et al. | |
| 9,012,668 B2 | 4/2015 | Winsness | |
| 9,061,987 B2 | 6/2015 | Bootsma | |
| 9,108,140 B2 | 8/2015 | Winsness | |
| 9,169,498 B2 | 10/2015 | Woods et al. | |
| 9,212,334 B2 | 12/2015 | Cantrell et al. | |
| 9,290,728 B2 | 3/2016 | Bootsma | |
| 9,320,990 B2 | 4/2016 | Winsness | |
| 9,328,311 B2 | 5/2016 | Jenkins et al. | |
| 9,340,767 B2 | 5/2016 | Narendranath | |
| 9,353,332 B2 | 5/2016 | Lewis et al. | |
| 9,375,731 B2 | 6/2016 | Dieker et al. | |
| 9,714,267 B2 | 7/2017 | Emanuele et al. | |
| 9,745,540 B2 | 8/2017 | Sungail et al. | |
| 9,896,643 B2 | 2/2018 | Redford | |
| 2004/0087808 A1 | 5/2004 | Prevost et al. | |
| 2007/0036881 A1 | 2/2007 | Griffith | |
| 2007/0141691 A1 * | 6/2007 | Hirl | C05F 5/008 |
| | | | 435/161 |
| 2007/0238891 A1 | 10/2007 | Winsness et al. | |
| 2007/0254089 A1 * | 11/2007 | Hickey | C12F 3/10 |
| | | | 426/624 |
| 2008/0110577 A1 | 5/2008 | Winsness | |
| 2008/0193991 A1 | 8/2008 | Allen et al. | |
| 2008/0277264 A1 | 11/2008 | Sprague | |
| 2009/0176289 A1 * | 7/2009 | Friedmann | C12M 21/04 |
| | | | 435/167 |
| 2009/0250412 A1 | 10/2009 | Winsness et al. | |
| 2010/0159519 A1 | 6/2010 | Diner et al. | |
| 2010/0221804 A1 | 9/2010 | Veit et al. | |
| 2010/0281765 A1 | 11/2010 | Schwartz | |
| 2011/0086149 A1 | 4/2011 | Bootsma | |
| 2011/0143411 A1 | 6/2011 | Yuan et al. | |
| 2013/0295661 A1 * | 11/2013 | Roesch | B01D 3/002 |
| | | | 435/297.1 |
| 2014/0273166 A1 | 9/2014 | Narendranath | |
| 2015/0037857 A1 | 2/2015 | Redford | |
| 2015/0152372 A1 | 6/2015 | Kohl et al. | |
| 2016/0145650 A1 | 5/2016 | Lewis et al. | |
| 2016/0152931 A1 | 6/2016 | Bootsma | |
| 2017/0051322 A1 | 2/2017 | Bushong et al. | |

OTHER PUBLICATIONS

Hirl. "Waste Streams and Anaerobic Digestion, Minnesota Opportunities", Stanley Consultants, Dec. 2, 2009, Published online at [http:www.extension.umn.edu/biorenewables/pdfs/7-Hirl%20AD%UofMNOV30vers.pdf], 23 pages.

Hunt, et al. "Corn Stillage as a Feedstuff for Broilers and Turkeys", Applied Poultry Science, Inc., Research Report 1997, published online at [http://japr.fass.org/content/6/3/310.full.pdf], 9 pages.

International Search Report and Written Opinion for PCT Application Serial No. PCT/US2012/033346, dated Sep. 20, 2012, 20 pages.

European Search Report for European Application No. EP12774824.2 dated Jan. 26, 2015, 5 pages.

Non-Final Office Action for U.S. Appl. No. 14/112,897 dated May 21, 2015, 26 pages.

"Thin Stillage Solids Separation System", retrieved on Jun. 26, 2018 via http://www.icminc.com/products/thin-stillage-solids-separation-system.html, (2 pages).

"About Harvesting Technology: Bringing Profitable Innovation for Ethanol Production", retrieved on Jun. 26, 2018 via http://harvestingtech.com/#benefits, (11 pages).

* cited by examiner

Table 1 Experimental Compositions of Stillage Fractions

|         | Moisture | Protein  | Fiber              | Fat    | Ash                    |
|---------|----------|----------|--------------------|--------|------------------------|
| Oil     | 0.9%     | 3.03% FFA| <0.01% insolubles  | 98.0%  | 1.13% unsaponifiables  |
| Syrup   | 31.6%    | 10.9%    | 0.1%               | 8.2%   | 6.1%                   |
| Protein | ND       | 58.6%    | <1%                | 12.6%  | ND                     |
| Fiber   | ND       | 26.0%    | 10%                | 3.5%   | 0.7%                   |

FIG. 5

Table 2. Expected Compositional Ranges of Comercial Stillage Fractions

|         | Moisture | Protein    | Fiber               | Fat    | Ash                   |
|---------|----------|------------|---------------------|--------|-----------------------|
| Oil     | 0.5-1%   | 2-5 % FFA  | 0-0.5% insolubles   | 97-99% | 0.5-2% unsaponifiables|
| Syrup   | 30-40%   | 10.9%      | 0-1%                | 6-10%  | 5-7%                  |
| Protein | 8-12%    | 45-55%     | 1-5%                | 12.6%  | 1-3%                  |
| Fiber   | 8-12%    | 15-20%     | 8-12%               | 2-5%   | 1-2%                  |

FIG. 6

SYSTEMS AND METHODS FOR STILLAGE FRACTIONATION

CROSS-REFERENCE

This application is a Division of application Ser. No. 14/112,897 filed Oct. 18, 2013, which is a U.S. national stage filing of Patent Cooperation Treaty (PCT) application serial number PCT/US2012/033346 entitled "SYSTEMS AND METHODS FOR STILLAGE FRACTIONATION" filed on Apr. 12, 2012, which claims the benefit of U.S. Provisional Application Ser. No. 61/476,702, filed Apr. 18, 2011, and entitled "SYSTEMS AND METHODS FOR STILLAGE FRACTIONATION", the entirety of which are expressly incorporated herein by reference.

FIELD

The subject disclosure relates to systems and methods for fractionating thin and whole stillage in an ethanol production facility.

BACKGROUND

Ethanol traditionally has been produced from grain-based feedstocks (e.g., corn, sorghum/milo, barley, wheat, soybeans, etc.), or from sugar (e.g., sugar cane, sugar beets, etc.).

In a conventional ethanol plant, corn, sugar cane, other grain, beets, or other plants are used as a feedstock and ethanol is produced from starch contained within the corn, or other plant feedstock. In the case of a corn facility, corn kernels are cleaned and milled to prepare starch-containing material for processing. Corn kernels can also be fractionated to separate the starch-containing material (e.g., endosperm) from other matter (such as fiber and germ). Initial treatment of the feedstock varies by feedstock type. Generally, however, the starch and sugar contained in the plant material is extracted using a combination of mechanical and chemical means.

The starch-containing material is slurried with water and liquefied to facilitate saccharification, where the starch is converted into sugar (e.g., glucose), and fermentation, where the sugar is converted by an ethanologen (e.g., yeast) into ethanol. The fermentation product is beer, which comprises a liquid component, including ethanol, water, and soluble components, and a solids component, including unfermented particulate matter (among other things). The fermentation product is sent to a distillation system where the fermentation product is distilled and dehydrated into ethanol. The residual matter (e.g., whole stillage) comprises water, soluble components, oil, and unfermented solids (e.g., the solids component of the beer with substantially all ethanol removed, which can be dried into dried distillers grains (DDG) and sold, for example, as an animal feed product). Other co-products (e.g., syrup and oil contained in the syrup) can also be recovered from the whole stillage.

In a typical ethanol plant, a massive volume of whole stillage is generally produced. In fact, for a typical ethanol plant the amount of whole stillage produced can be nearly 13.4 gallons per bushel of corn processed. Roughly, a third of the corn feedstock is present in the whole stillage as dissolved and suspended solids. The stillage contains almost 90% water. Whole stillage is responsible for a substantial portion of the wastewater generated by ethanol plants. The financial cost of the water, its treatment and disposal (typically through evaporation) can be significant.

While stillage is typically viewed as a liability for an ethanol plant, it is possible to generate a number of high value co-products from the stillage. For example, oil in stillage, high protein feeds, and syrups are all able to be generated from stillage and sold as higher value co-products. Currently, in the interest of improving efficiencies of ethanol plants, whole stillage is often separated into two components: a solid component and a liquid component. Separation may be performed using centrifugation, or filter and press. The solid component may be dried to generate dried distillers grain (DDG) which is sold as animal feed. The liquid component, known as thin stillage, may be dried and used to increase the fat content of DDG to make DDGS (Distillers Dried Grains with Solubles). This process requires the drying of a large amount of water, which is very energy intensive and costly. Thin stillage may also be recycled into the plant, such as for replacement of some portion of the water used during fermentation (fermentation backset).

Further, there is currently a strong push to generate corn oil from stillage, as oil is a particularly high value commodity, and for regulatory and legal considerations. Ideally, an ethanol plant would generate a minimum of 1.33 pounds of oil product per bushel of corn processed. A number of oil recovery methods are known, but to date none has achieved more than about one pound of oil per bushel. Further, conventional processes for recovering oil from fermentation products often sacrifice oil quality such that the oil contains high levels of free fatty acids. The presence of a high level of free fatty acids can hamper the production of end products such as, for example, the yield and quality of any bio-diesel eventually produced with the oil as a feedstock.

For example, the patent application PCT/US2009/045163 (entitled "METHODS FOR PRODUCING A HIGH PROTEIN CORN MEAL FROM A WHOLE STILLAGE BYPRODUCT AND SYSTEM THEREFORE") discloses a process for separating whole stillage into a solid portion and a thin stillage. The thin stillage is again separated to a protein and a water-soluble portion. An oil fraction may be separated from the water portion via evaporation. In the method of the PCT application, oil is recovered post evaporation, which likely results in yield reductions and oil quality sacrifices.

Another current method of oil recovery is disclosed by U.S. Pat. No. 7,829,680 (entitled "SYSTEM AND METHOD FOR ISOLATION OF GLUTEN AS A CO-PRODUCT OF ETHANOL PRODUCTION"). In this method, a plurality of screens is utilized to separate a fiber product from an oil/protein product. The oil and protein may then be separated via centrifugation.

While these known systems and methods may generate valuable co-products from ethanol production stillage, they have inherent drawbacks related to oil quality, quantity of oil recovered, water balance issues, and composition of the protein products isolated.

SUMMARY

The disclosed aspects relate to systems and methods for fractionating whole stillage from an ethanol production facility. The system of fractionation generates multiple valuable co-products while reducing the demand for energy over many traditional methods of treatment of stillage.

In the disclosed systems and methods, the whole stillage undergoes a separation of its liquid portion (thin stillage) from its solid portion (fiber cake). This separation may be performed utilizing membranes, screw presses, centrifuges, or other suitable means. In some embodiments, the solids and liquids in whole stillage may be separated utilizing a screening centrifuge.

The fiber cake may be dried to generate a high fiber animal feed. The thin stillage may be provided to a three-phase separator for separation into an oil emulsion, an aqueous clarified stillage, and a protein paste. In some embodiments, the three-phase separator may include a disk nozzle centrifuge or other suitable separator device.

The protein paste may be dried to generate a high protein animal feed. In some cases, this feed may have greater than about 45% protein content. In alternate embodiments, the protein paste may be returned to the fiber cake prior to drying in order to alter the nutritional makeup of the animal feed produced.

The clarified thin stillage may be utilized as fermentation backset, or other makeup water source, within an ethanol production facility, for example. Alternatively, some or all of the clarified stillage may be condensed, utilizing an evaporator or other suitable device, to yield a syrup. The syrup (high solid syrup) may be utilized as an animal feed product. Generally, the syrup may contain between about 30% and about 40% moisture, greater than about 10% protein, less than about 1% fiber, between about 6% and about 10% fat, and between about 5% to about 7% ash.

The oil emulsion may be subjected to a pH adjustment to liberate the oil from the emulsion. The pH adjustment may utilize a caustic to bring the emulsion pH to about 8.0 to about 8.5. The oil can be separated from the emulsion utilizing a centrifuge, or other suitable separating device. The oil resulting may include greater than about 97% fat. Further, in some embodiments, about 1.33 or more pounds of oil may be recovered from the whole stillage generated from processing a bushel of corn for ethanol.

Note that the various features of the various aspects described above may be practiced alone or in combination. These and other features will be described in more detail below in the detailed description and in conjunction with the following figures.

DESCRIPTION OF THE DRAWINGS

In order that the various aspects may be more clearly ascertained, some embodiments will now be described, by way of example, with reference to the accompanying drawings, in which:

FIG. 5 contains TABLE 1 which lists experimental compositions of stillage fractions, in accordance with some embodiments; and FIG. 6 contains TABLE 2 which lists expected compositions of commercially derived stillage fractions, in accordance with some embodiments.

DESCRIPTION OF THE EMBODIMENTS

The various aspects will now be described in detail with reference to several embodiments thereof as illustrated in the accompanying drawings. In the following description, numerous specific details are set forth in order to provide a thorough understanding of the various aspects. It will be apparent, however, to one skilled in the art, that embodiments may be practiced without some or all of these specific details. In other instances, well known process steps and/or structures have not been described in detail in order to not unnecessarily obscure the disclosed aspects. The features and advantages of embodiments may be better understood with reference to the drawings and discussions that follow.

The following description relates to systems and methods for fractionating stillage from an ethanol production plant or other processing facility. Ethanol plants generate large quantities of stillage as a low value product. Stillage is generally a low value co-product that requires substantial energy to dry into solubles for addition to distillers dried grains, or must be disposed of in some other manner. There is the potential for the generation of high value co-products from stillage, thus, the disclosed aspects provide for systems and methods that improve stillage utilization, which can generate multiple high quality co-products without unduly influencing the water balance of the ethanol production facility. Such systems and methods can provide increased revenue from co-products and a lower impact on the environment.

The disclosed systems and methods provide a means to substantially improve the quality and value of stillage by fractionating the stillage into components, each highly valued in their own right. The fractions generated by the disclosed systems and methods, in addition to being intrinsically valuable, provide an improved water balance for the ethanol production facility, thereby reducing the energy required to process the stillage over traditional evaporation and drying.

Figure 1:
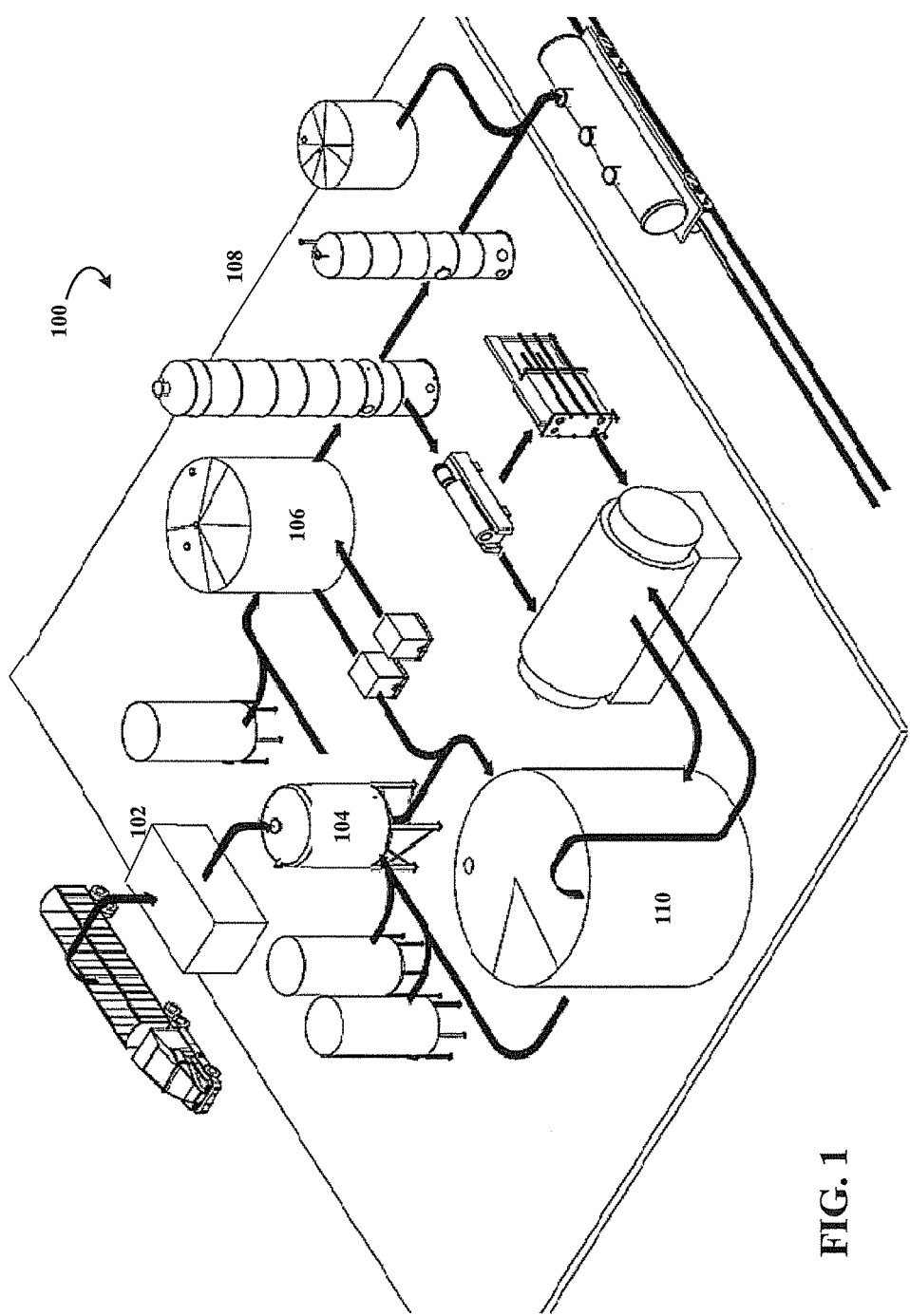
FIG. 1 is a perspective view of a biorefinery comprising an ethanol production facility, in accordance with some embodiments.

Referring to FIG. 1, an example biorefinery 100 comprising an ethanol production facility configured to produce ethanol from corn is shown. The example biorefinery 100 comprises an area 102 where corn (or other suitable material including, but not limited to, biomass, sugars, and other starch products) is delivered and prepared to be supplied to the ethanol production facility. The ethanol production facility comprises apparatus 104 for preparation and treatment (e.g., milling) of the corn into corn flour suitable for fermentation into fermentation product in a fermentation system 106. The ethanol production facility comprises a distillation system 108 in which the fermentation product is distilled and dehydrated into ethanol. The biorefinery may also comprise, in some embodiments, a by-product treatment system 110 (shown as comprising a centrifuge, a dryer, an evaporator, and associated tanks).

Figure 2A:
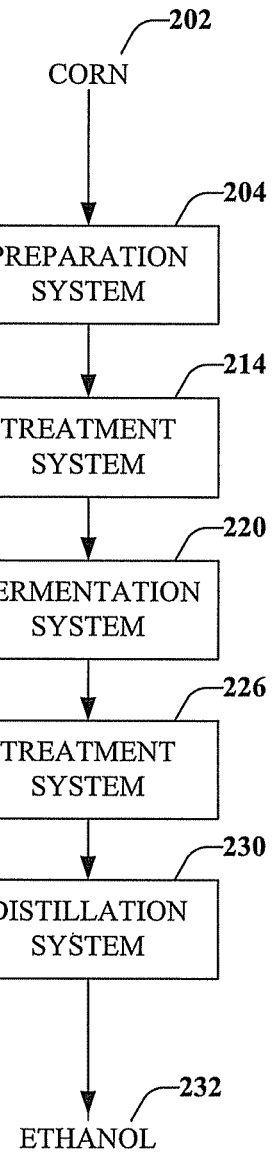
FIGS. 2A and 2B are process flow diagrams illustrating examples of ethanol production processes from corn to ethanol, in accordance with some embodiments.
Figure 2B:
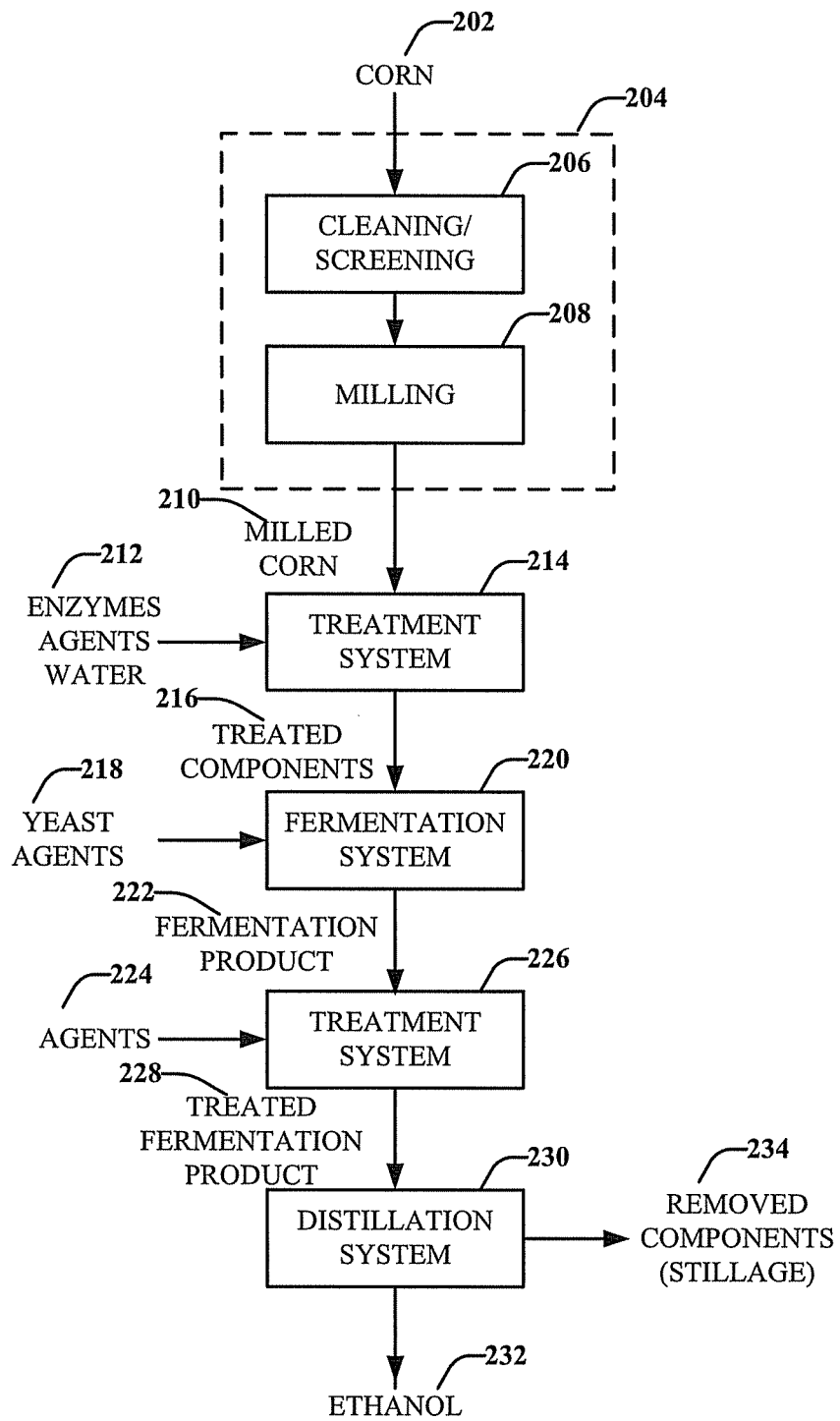

Referring to FIGS. 2A and 2B, in an ethanol production process, corn 202 (or other suitable feed material) may be prepared for further treatment in a preparation system 204. As illustrated in FIG. 2B, the preparation system 204 may comprise cleaning or screening 206 to remove foreign material, such as rocks, dirt, sand, pieces of corn cobs and stalk, and other unfermentable material (e.g., removed components). After cleaning or screening 206, the particle size of corn may be reduced by milling 208 to facilitate further processing. The corn kernels may also be fractionated into starch-containing endosperm, fiber, and germ, in accordance with some embodiments. The milled corn 210 or endosperm is slurried with water, enzymes and agents 212 to facilitate the conversion of starch into sugar (e.g. glucose), such as in a first treatment system 214. The sugar (e.g., treated component 216) is converted into ethanol by an ethanologen (e.g. yeast or other agents 218) in a fermentation system 220. The product of fermentation (fermentation product 222) is beer, which comprises a liquid component, including ethanol and water and soluble components, and a solids component, including unfermented particulate matter (among other things). The fermentation product may be treated with agents 224 in a second treatment system 226. The treated fermentation product 228 is sent to a distillation system 230. In the distillation system 230, the (treated) fermentation product is distilled and dehydrated into ethanol 232. In some embodiments, the removed components 234 (e.g., whole stillage), which comprise water, soluble components, oil, and unfermented solids (e.g., the solids component of the beer with substantially all ethanol removed), may be dried into dried distillers grains (DDG) in a third treatment system (where the removed components may be treated with agents) and sold as an animal feed product. Other co-products, for example, syrup (and oil contained in the syrup), may also be recovered from the stillage, as will be described in further detail below.

In some systems, the thin stillage that results when solids are removed from the whole stillage can be used as a backset during the fermentation process and also can be used to increase the fat content of DDGS (Distillers Dried Grains with Solubles). However, the addition of thin stillage to DDGS requires costly evaporation processes that increase the DDGS production cost. Disclosed herein are systems and methods for fractionating the whole stillage in order to generate relevant quantities of valuable co-products in a manner which ultimately reduces the required fuel spent on evaporation.

Figure 3:
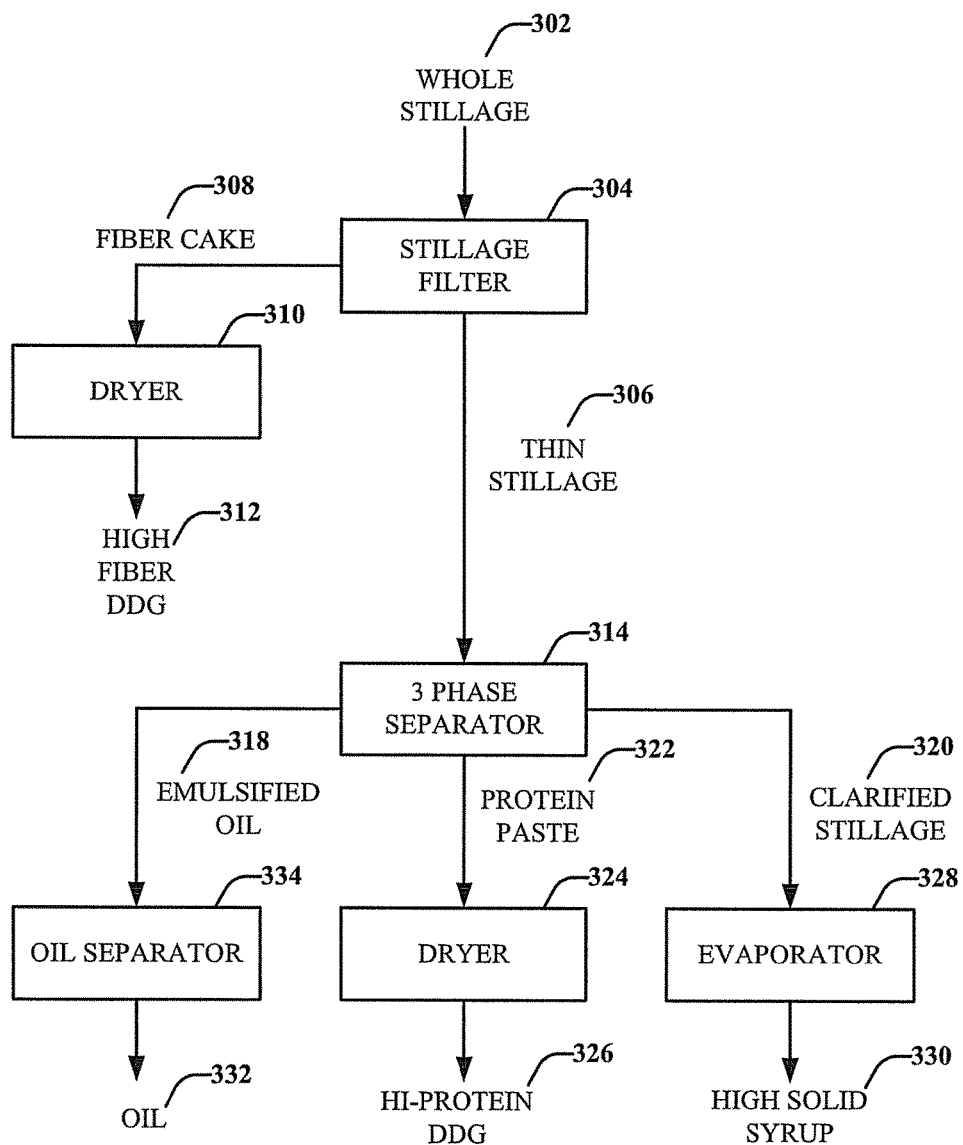
FIG. 3 is a schematic block diagram illustrating a system for fractionating stillage, in accordance with some embodiments.

Referring now to FIG. 3, an example schematic block diagram of a system for fractionation of the removed stillage component is provided. In this example diagram, the whole stillage 302 is provided to a stillage filter 304 for separation of the stillage into a solids component and a liquid thin stillage 306. The separation may be performed through screw press, centrifugation, decanters, or via filtration type methodologies. In some particular embodiments, the separation may be performed utilizing a screen bowl centrifuge. One of ordinary skill in the art will appreciate that the speed or amount of centrifugal force applied will depend on various factors such as sample size and may be adjusted appropriately depending on such factors. Suitable separators and centrifuges are available from various manufacturers such as, for example, Seital of Vicenza, Italy, Westfalia of Oelde, Germany or Alfa Laval of Lund, Sweden.

The solid component comprises a high fiber cake 308, which may be dried at a dryer 310 to a high fiber dried distillers grain (DDG) 312 product. Such high fiber DDG may be particularly suited for the poly-gastric animal feed markets (ruminant feed). In some embodiments, the fiber cake may additionally undergo a washing step prior to being dried. The wash fluid may be combined with the liquid thin stillage, in some embodiments.

Separation of the fiber cake solids from the thin stillage may be performed soon after initial production of the fermentation product (whole stillage) in order to maintain co-product composition quality and to prevent undue exposure of the co-products to heat, oxygen, and potential contaminants. If the whole or thin stillage is left exposed for extended periods of time in the presence of moisture, hydrolysis of the oils may occur which leads to the formation of free fatty acids, which degrades the quality of oil produced.

The resulting liquid thin stillage 306 is provided to a three phase separator 314, which may include a disk nozzle type centrifuge or suitable filtration type system. The three phase separator 314 separates the thin stillage 306 into a top layer of oil emulsion 318, a middle aqueous clarified thin stillage 320, and a protein paste 322. One of ordinary skill in the art will appreciate that the speed or amount of centrifugal force applied will depend on various factors such as sample size and may be adjusted appropriately depending on such factors. Suitable separators and centrifuges are available from at least the manufacturers listed above.

The protein paste 322 may be dried in a dryer 324 to a high protein DDG product 326. The high protein DDG may be particularly suited for mono-gastric (non-ruminant) and young animal feed. The high protein DDG may have high metabolize-able energy and a lysine content of between about 2% and about 3%, which can be important in feed ration formulations.

The clarified thin stillage 320 may be condensed through evaporation 328 or concentrated by reverse osmosis to yield high solid syrup 330. Due to low levels of suspended solids in the clarified thin stillage, high total solids can be achieved in a concentrated syrup without substantial viscosity limitations. The high solids syrup 330 may have between about 30 and 80 percent solids, dependent upon material handling properties desired, as well as end use. In some particular embodiments, the high solid syrup may contain greater than around 60% solids. High solid syrup 330 may be marketed as a high energy animal feed supplement. In alternate embodiments, some portion of the clarified thin stillage may be utilized as a backset for fermentation, thereby further reducing the need for evaporation further.

The oil emulsion 318 may be pH treated by an alkali in order to disrupt the emulsion. The adjustment of pH may be critical for the liberation of the oil from emulsion, and may result in greater oil yields and enhanced oil quality. Particularly, adjusting the pH of the oil fraction separates or breaks the oil fraction such that the resulting oil recovered has a low fatty acid content. The age of the fermented product and the organic acid content of the fermented product can affect the optimum pH for separation, however, the oil fraction is treated with the highest pH possible to reduce the overall free fatty acid content in the separated oil without sacrificing oil quality. In some embodiments, the pH is adjusted to a range of about 7 to about 10. In some particular embodiments, the pH is adjusted to between around 8.0 and around 8.5.

Oil 332 may be separated from the remaining emulsion/aqueous layer through centrifugation, filtration, distillation or other suitable separator 334. The remaining aqueous layer/emulsion may be high in protein and recycled for addition to DDG or sold as a separate feed product.

The oil composition recovered from the aspects described herein may be further processed in a variety of ways. For example, the crude oil may be filtered and bleached to provide a food grade oil for consumer use. In one embodiment, the crude oil may be degummed, further caustic refined, and subjected to a soap removal step according to commercially available processes. Following these steps, the oil may be subjected to one or more clay bleaching steps to achieve an oil of desired content and color. If one or more clay bleaching steps are used, the clay may be an acid clay or a non-acid clay. In one embodiment, the bleaching step may include, by way of example, an acid clay or a non-acid clay at around 1% to around 5% based on the total weight. In addition to or as an alternative to clay bleaching, after the crude oil has been degummed, caustic refined and subjected to a soap removal step, a food grade oil of a desired color may be achieved using a heat bleaching step.

The oil composition can be used in a wide variety of applications. Such exemplary applications include the areas of oleochemicals, feed (e.g., animal feed) as well as oils suitable for human consumption. Oleochemicals include feedstock chemicals that are suitable for biodiesel production (fatty acid methyl esters). Industrial oleochemicals are useful in the production of soaps, detergents, wire insulation, industrial lubricants, leather treatments, cutting oils, mining agents for oil well drilling, ink removal, plastic stabilizers, ink, and in rubber production. Other industrial applications include waxes, shampoos, personal hygiene and food emulsifier or additive products. It is also possible in some embodiments, to pre-treat oil for downstream uses, such as conversion to bio-diesel.

The recovered oil composition can contain low levels of moisture, insolubles and unsaponifiables (MIU content). Moisture, as contemplated herein, includes water and any volatile material such as, for example, hexane, ethanol, methanol, or a combination thereof. Insoluble matter (i.e., "insolubles"), as contemplated herein, refers to and includes any matter incapable of being dissolved in the aqueous portion, oil fraction or oil composition. Unsaponifiable matter (i.e., "unsaponifiables") includes any variety of possible non-triglyceride materials that act as contaminants during bio-diesel production. Usaponifiable matter can significantly reduce the end product yields of the oil composition and can, in turn, reduce end product yields of processes such as, for example, bio-diesel production processes.

Maintaining low levels of moisture is especially desirable because moisture fosters the formation of free fatty acids instead of esters. In one embodiment, the oil composition contains no greater than around 1% w/w of total moisture content, alone, based on the total weight of the oil composition. In some embodiments, the moisture content, alone, is no greater than about 0.5% w/w or about 0.1% w/w.

In one embodiment, the oil composition comprises no greater than approximately 3% w/w of unsaponifiables, based on the total weight of the oil composition. In some embodiments, the oil composition comprises no greater than around 2% w/w or around 1% w/w of unsaponifiables.

In one embodiment, the oil composition contains no greater than about 1% w/w insolubles, alone, based on the total weight of the oil composition. In some embodiments, the insolubles content, alone, is no greater than approximately 0.5% w/w or approximately 0.1% w/w.

The oil composition may, in some embodiments, exhibit an iodine value acceptable for bio-diesel production and, in some embodiments, exhibits an iodine value higher than that expected from a neat oil sample. The oil can further comprise various carotene, carotenoid, and antioxidant or neutraceutical compounds.

In one embodiment, the oil composition contains no greater than about 5% w/w free fatty acid content, based on the total weight of the oil composition. In some embodiments, the free fatty acid content, is no greater than around 3% w/w.

The fatty acid content of the oil composition is comprised of various fatty acids known in the art. In one embodiment, the oil composition comprises C 16 palmitic acid which represents no greater than about 15% w/w of the total fatty acid content, based on the total weight of the oil composition. In another embodiment, the C 16 palmitic acid content is no greater than around 10% w/w of the total fatty acid content. In one embodiment, the oil composition comprises C 18 stearic acid which represents at least about 3% w/w of the total fatty acid content, based on the total weight of the oil composition. In another embodiment, the C 18 stearic acid content is at least about 1.5% w/w of the total fatty acid content. In one embodiment, the oil composition comprises C18-1 oleic acid which represents at least around 30% w/w of the total fatty acid content, based on the total weight of the oil composition. In another embodiment, the C18-1 oleic acid content is at least about 25% w/w of the total fatty acid content. In one embodiment, the oil composition comprises C18-2 linoleic acid which represents at least around 60% w/w of the total fatty acid content, based on the total weight of the oil composition. In another embodiment, the C 18-2 linoleic acid content is at least around 50% w/w of the total fatty acid content. In one embodiment, the oil composition comprises C18-3 linolenic acid which represents no greater about 1.5% w/w of the total fatty acid content, based on the total weight of the oil composition. In another embodiment, the C18-3 linolenic acid content is no greater than about 0.5% w/w of the total fatty acid content.

Since the entire thin stillage is not evaporated, in these embodiments, there is substantial fuel and cost savings over traditional stillage handling which includes the substantial evaporation of the thin stillage for addition back to the DDG to generate dried distillers grains with solubles (DDGS). As such, not only are greater quantities of higher value products generated through the disclosed treatment of the whole stillage, but additionally, the process utilizes less fuel thereby reducing pollution generated and reducing operational costs.

Figure 4:
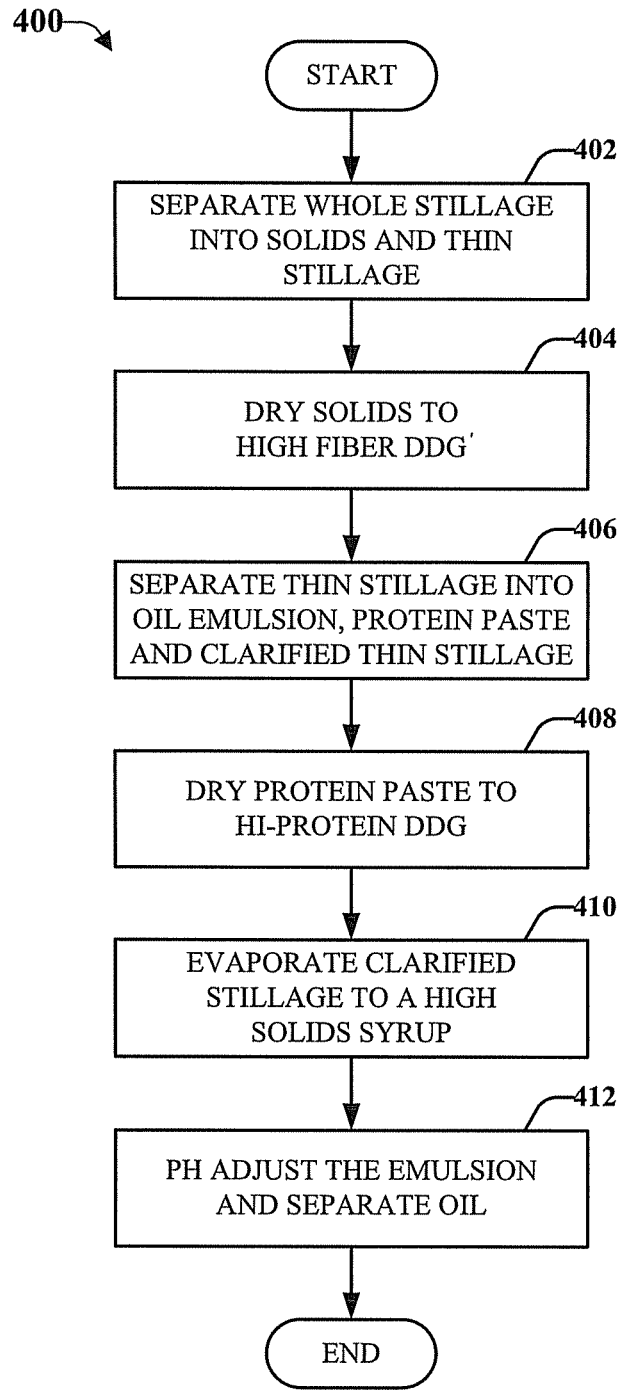
FIG. 4 is an example flowchart illustrating a process of fractionating stillage into valuable co-products, in accordance with some embodiments.

FIG. 4 provides an example flow diagram 400 for the process of generating high value co-products. In this process, the whole stillage is separated into solids and the liquid thin stillage (at 402). The solids include a fiber cake which is dried (at 404) to a high fiber dried distiller grain (HF-DDG) co-product.

In some embodiments, due to the composition of the fiber cake, there is less water retention of the product after separation of the thin stillage and washing. As the fiber cake includes less water, there is a substantial reduction in drying costs associated with the production of the high fiber dried distiller grain (HF-DDG) co-product over a more traditional DDG product. In some embodiments, the solid content of the fiber cake may be as high as between around 40% to around 45% solids before drying, as opposed to a wet cake (used to make conventional DDG) which typically includes only about 30% to around 35% solids prior to drying.

In some embodiments, the thin stillage is fractionated (at 406) into an oil emulsion, a protein paste, and a clarified thin stillage. The protein paste, which includes a high lysine content, is dried (at 408) to generate a high protein dried distillers grain (DDG HP). In some embodiments, the protein paste may also be returned to the fiber cake and dried together to generate an enhanced DDG product. Handling of the protein paste may be determined by market considerations, and equipment available at the ethanol production facility.

The thin stillage may then be condensed (at 410) to a high solids content (e.g., between around 30 to 80 percent solids) to generate a high solids syrup. High solids syrups are usable as an effective animal feed substitute, however the generation of practical high solid syrup may be difficult to obtain. This is because most syrups generated from thin stillage, once the solid content approaches about 30 percent, become prohibitively viscous, and are unusable as a marketable co-product. By processing the thin stillage to a clarified thin stillage, ultra high solids content (e.g., greater than about 30%) is achievable in a syrup which retains a viscosity of molasses. Thus, the co-product is easily transported and handled by prospective buyers.

Lastly, the oil emulsion is treated to extract valuable oil (at 412). Oil extraction is facilitated by pH adjusting the emulsion with an alkali. The addition of the caustic agent disrupts the emulsion and liberates the oil. The liberated oil may be extracted from the remaining emulsion via decanting, centrifugation, filtration or other suitable method. In some embodiments, greater than about 1.33 pounds of corn oil are achieved per bushel of corn utilizing the disclosed embodiments.

A series of limited examples were conducted according to an exemplary embodiment of the system (as shown in FIG. 3) in an effort to determine suitable apparatus and operating conditions for the fractionation of whole stillage. The following examples are intended to provide clarity to some embodiments of systems and means of operation; given the limited nature of these examples, they do not limit the scope of the disclosed aspects.

EXAMPLE 1

In this example experiment, whole stillage was screened utilizing a screen centrifuge in order to obtain a fiber cake and thin stillage. The fiber cake was dried and tested for composition. The thin stillage was further processed by decanter centrifuge to yield an oil emulsion, clarified thin stillage and a protein paste. The protein paste was dried. The clarified thin stillage was evaporated to over 60% solids content. The oil emulsion was treated using a caustic agent to adjust the pH to about 8. The oil emulsion was again subjected to centrifugation in order to remove the oil form emulsion. The oil, dried protein paste and high solid syrup were then subjected to compositional analysis. The results of this analysis are provided in relation to TABLE 1 of FIG. 5.

In summary, the oil product had 0.9% moisture content, 3.03% free fatty acids (FFA), <0.01% insolubles, and 1.13% unsaponifiables. The high solids syrup composition was 31.6% moisture, 10.9% protein, 0.1% fiber, 6.1% ash, and 8.2% fat. The protein paste composition was 58.6% protein, 12.6% fat, and <1% fiber. The high fiber DDG composition was 26.0% protein, 10% fiber, 3.5% fat, and 0.7% ash.

The yields of the four products on a percentage basis are approximately 9% oil, 13% syrup, 40% protein, and 38% fiber. These yields correspond to 1.3 lb oil, 2 lb syrup, 6 lb protein, and 6 lb fiber on a pound per bushel basis. The yields expected can lead to changes to the expected compositions due to tradeoffs between yield and purity. The expected compositional ranges from commercial production of these products are show in TABLE 2 of FIG. 6.

The embodiments as disclosed and described in the application (including the FIGURES and Examples) are intended to be illustrative and explanatory. Modifications and variations of the disclosed embodiments, for example, of the apparatus and processes employed (or to be employed) as well as of the compositions and treatments used (or to be used), are possible; all such modifications and variations are intended to be within the scope of the various aspects presented herein.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

Reference throughout this specification to "one aspect," or "an aspect," or "one embodiment," or "an embodiment" means that a particular feature, structure, or characteristic described in connection with the aspect or embodiment is included in at least one aspect or one embodiment. Thus, the appearances of the phrase "in one aspect," or "in an aspect," or "in one embodiment," or "in an embodiment" in various places throughout this specification can, but are not necessarily, referring to the same aspect or embodiment, depending on the circumstances. Furthermore, the particular features, structures, or characteristics may be combined in any suitable manner in one or more aspects or embodiments.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

What is claimed is:

1. An ethanol plant that processes whole stillage comprising:
    a fermentation apparatus for making a fermentation product;
    a distillation apparatus adapted to separate ethanol from the fermentation product and form whole stillage;
    a first separator for separating a thin stillage liquid output from the whole stillage, wherein the first separator comprises a centrifuge;
    a second separator for separating a clarified liquid stillage output from at least a portion of the thin stillage liquid output, wherein said second separator comprises a centrifuge;
    and
    a connection for recycling a portion of the clarified liquid stillage output upstream for utilization as fermentation backset.

2. The ethanol plant of claim 1, wherein the first separator produces a high fiber wet cake.

3. The ethanol plant of claim 2 further comprising:
    a cake dryer for drying the high fiber wet cake to provide a high fiber animal feed product.

4. The ethanol plant of claim 3, wherein the solid content of the high fiber wet cake is between 40% and 45% before drying.

5. The ethanol plant of claim 1 further comprising an evaporation apparatus or a reverse osmosis system for condensing a portion of the clarified liquid stillage to form a syrup.

6. The ethanol plant of claim 1 wherein the clarified liquid stillage contains less unfermentable solids than the thin stillage liquid.

7. The ethanol plant of claim 1 further comprising an evaporation apparatus for condensing a portion of the thin stillage liquid output.

8. An ethanol plant that processes whole stillage comprising:
    a fermentation system adapted to produce a fermentation product;
    a distillation system in fluid communication with the fermentation system, wherein the distillation system is adapted to separate ethanol from the fermentation product and form whole stillage;
    a first centrifugation separation system in fluid communication with the distillation system, wherein the first centrifugation separation system is adapted to separate the whole stillage into wet cake and thin stillage output; and a second centrifugation separation system in fluid communication with the first centrifugation separation system, wherein the second centrifugation separation system is adapted to separate at least a portion of the thin stillage output into an aqueous fraction output, an oil emulsion fraction, and a protein fraction, wherein the aqueous fraction output is in fluid communication with the fermentation system for utilization as backset.

9. The ethanol plant of claim 8, further comprising:
a paste dryer for drying the protein fraction to provide a high protein animal feed product.

10. The ethanol plant of claim 8 further comprising: a third centrifugation separation system in fluid communication with the oil emulsion fraction and adapted to separate oil from the oil emulsion fraction.

* * * * *